US009375149B2

(12) United States Patent
Lane et al.

(10) Patent No.: US 9,375,149 B2
(45) Date of Patent: Jun. 28, 2016

(54) NONCONTACT THERMOMETRY SYSTEMS AND METHODS

(71) Applicant: Welch Allyn, Inc., Skaneateles Falls, NY (US)

(72) Inventors: John A. Lane, Weedsport, NY (US); Jennifer M. Grant, Syracuse, NY (US); Matthew J. Kinsley, Liverpool, NY (US); Matthew D. Mullin, Memphis, NY (US); Nick H. Nguyen, Rochester, NY (US); David E. Quinn, Auburn, NY (US); Alisa R. Salibra, Fayetteville, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 90 days.

(21) Appl. No.: 14/218,710

(22) Filed: Mar. 18, 2014

(65) Prior Publication Data
US 2015/0265159 A1 Sep. 24, 2015

(51) Int. Cl.
*A61B 5/00* (2006.01)
*A61B 5/01* (2006.01)

(52) U.S. Cl.
CPC . *A61B 5/01* (2013.01); *A61B 5/015* (2013.01); *Y10T 29/49004* (2015.01)

(58) Field of Classification Search
CPC .................................. A61B 5/01; A61B 5/015
USPC ........................................................ 600/549
See application file for complete search history.

(56) References Cited

U.S. PATENT DOCUMENTS

| 5,693,247 | A | 12/1997 | Bu et al. | |
|---|---|---|---|---|
| 7,479,116 | B2 * | 1/2009 | Yarden | A61B 5/01 374/E1.011 |
| 8,317,720 | B2 * | 11/2012 | Laurence | A61B 5/01 119/51.02 |
| 8,452,382 | B1 | 5/2013 | Roth | |
| 8,836,598 | B2 * | 9/2014 | Shylo | A61B 5/015 343/762 |
| 8,948,850 | B2 * | 2/2015 | Roth | A61B 5/6887 600/309 |
| 8,971,998 | B2 * | 3/2015 | Messano, Jr. | A61B 5/0093 600/473 |
| 9,167,972 | B2 * | 10/2015 | Saint Clair | A61B 5/015 |
| 2010/0329301 | A1 | 12/2010 | Pang et al. | |
| 2013/0083823 | A1 | 4/2013 | Harr et al. | |
| 2014/0046192 | A1 | 2/2014 | Mullin et al. | |

OTHER PUBLICATIONS

International Search Report and Written Opinion for Application No. PCT/US2015/020664, mailed on Jun. 19, 2015, 14 pages.

\* cited by examiner

*Primary Examiner* — Max Hindenburg

(57) ABSTRACT

A method of determining a temperature of a patient includes determining that a temperature measurement device is located within at least one of a distance range and an alignment range of a portion of a measurement site of the patient, providing an indication to a user of the device that the device is located within the at least one of the distance range and the alignment range, and determining, with the device, a first temperature of a first location on the portion of the measurement site without contacting the patient with the device. Such a method also includes determining, with the device, a second temperature of a second location on the portion of the measurement site without contacting the patient with the device, wherein the second location is different from the first location. Such a method further includes determining a third temperature of the patient based on the first and second temperatures.

19 Claims, 5 Drawing Sheets

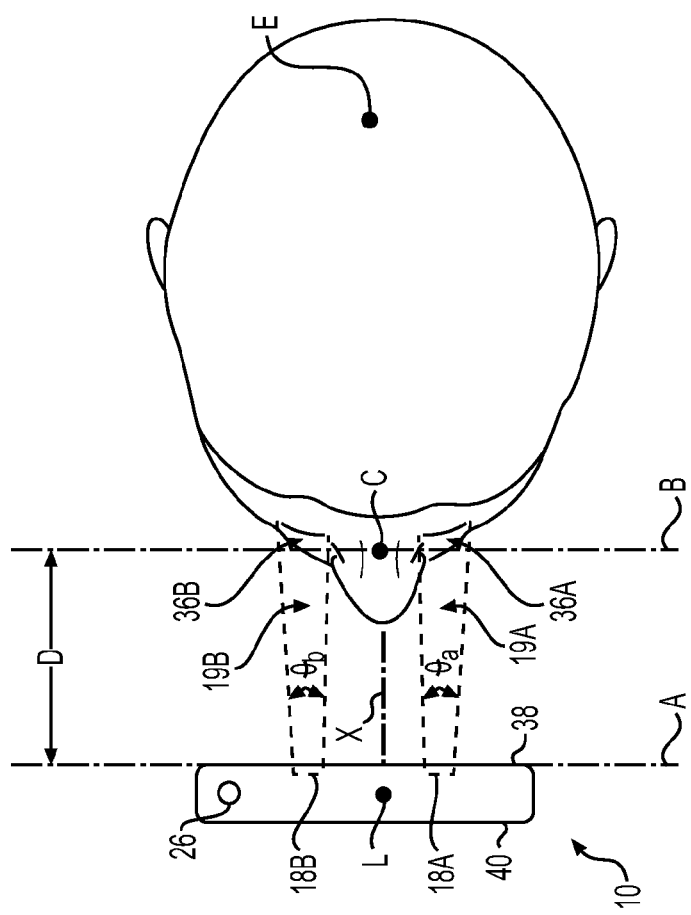
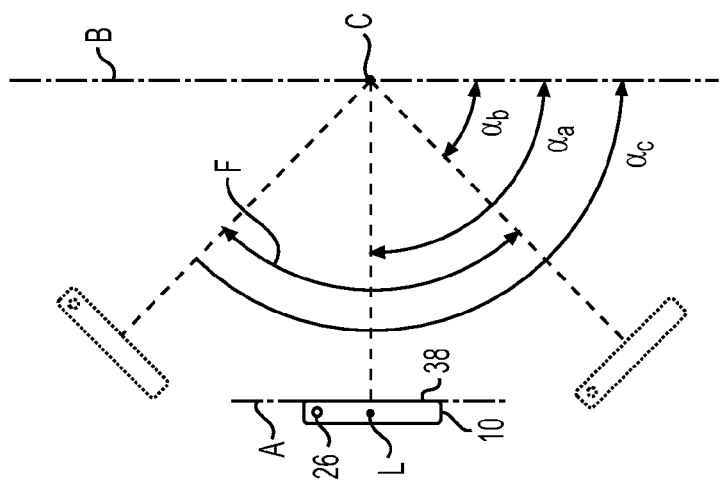
FIG. 4
FIG. 5

NONCONTACT THERMOMETRY SYSTEMS AND METHODS

FIELD OF THE INVENTION

The present disclosure relates to systems and methods for temperature determination and, in particular, to systems and methods for determining a patient's core temperature.

BACKGROUND OF THE INVENTION

Temperature is an important vital sign in patient evaluation. Physicians commonly use a variety of methods for determining patient temperature including, for example, obtaining temperature measurements with a thermometer. While thermometers utilizing mercury have been in existence for many years, modern thermometers typically employ one or more electronic sensors configured to measure patient temperature. Such sensors may take one or more measurements over a relatively short period of time. Based on these measurements, the thermometer may generate an estimated internal and/or core temperature of the patient.

Existing non-contact thermometers typically employ a sensing element configured to measure the temperature of, for example, the patient's forehead, temple, and/or other external body surfaces without contacting these surfaces, and to estimate the patient's core temperature based on such measurements. Such non-contact thermometers are described in co-owned U.S. patent application Ser. No. 13/450,446, the entire disclosure of which is incorporated herein by reference. While the accuracy of measurements taken with existing non-contact thermometers is highly dependent upon the distance and alignment of the device relative to the external body surface, such thermometers are typically not configured to assist the user in properly orienting the device prior to measurement. Thus, measurements taken with such devices are prone to significant error, and existing non-contact thermometers are not highly reliable as a means of patient evaluation.

The example embodiments of the present disclosure are directed toward overcoming at least the deficiencies described above.

SUMMARY

In an example embodiment of the present disclosure, a method of determining a temperature of a patient includes determining that a temperature measurement device is located within at least one of a distance range and an alignment range of a first portion of a measurement site of the patient, providing an indication to a user of the device that the device is located within the at least one of the distance range and the alignment range, and determining, with the device, a first temperature of a first location on at least one of the first portion and a second portion of the measurement site, without contacting the patient with the device. Such a method also includes determining, with the device, a second temperature of a second location on at least one of the first portion and the second portion of the measurement site, without contacting the patient with the device, wherein the second location is different from the first location. Such a method further includes determining a third temperature of the patient based on the first and second temperatures.

In another embodiment of the present disclosure, a temperature measurement device includes a first sensor configured to determine that the device is located within at least one of a distance range and an alignment range of a first portion of a measurement site of a patient, and at least one additional sensor configured to determine a first temperature of a first location on at least one of the first portion and a second portion of the measurement site and a second temperature of a second location on at least one of the first portion and the second portion of the measurement site. In such a device, the at least one additional sensor determines the first and second temperatures without contacting the patient, and the first and second temperatures are determined in response to the first sensor determining that the device is located within the at least one of the distance range and the alignment range. Such a device further includes a controller in communication with the first sensor and the at least one additional sensor. The controller is programmed to determine a third temperature of the patient based on the first and second temperatures.

In still another embodiment of the present disclosure, a method of manufacturing a temperature measurement device includes providing a first sensor configured to determine that the device is located within at least one of a distance range and an alignment range of a first portion of a measurement site of a patient, and providing at least one additional sensor configured to determine a first temperature of a first location on at least one of the first portion and a second portion of the measurement site and a second temperature of a second location on at least one of the first portion and the second portion of the measurement site. In such device the at least one additional sensor determines the first and second temperatures without contacting the patient, and the first and second temperatures are determined in response to the first sensor determining that the device is located within the at least one of the distance range and the alignment range. Such a method also includes providing a controller in communication with the first sensor and the at least one additional sensor, and programming the controller to determine a third temperature of the patient based on the first and second temperatures.

In yet another example embodiment, a method of determining a temperature of a patient includes determining that a temperature measurement device is located within at least one of a distance range and an alignment range of a portion of a measurement site of the patient, providing an indication to a user of the device that the device is located within the at least one of the distance range and the alignment range, and determining, with the device, a temperature from an inner-canthal region of the patient, without contacting the patient with the device. The method also includes determining a core temperature of the patient based on the temperature.

BRIEF DESCRIPTION OF THE DRAWINGS

FIG. 4 illustrates a third view of the temperature measurement device shown in FIG. 2.

FIG. 5 is a schematic diagram illustrating various positions of an example temperature measurement device relative to a plane.

DETAILED DESCRIPTION

Figure 1:
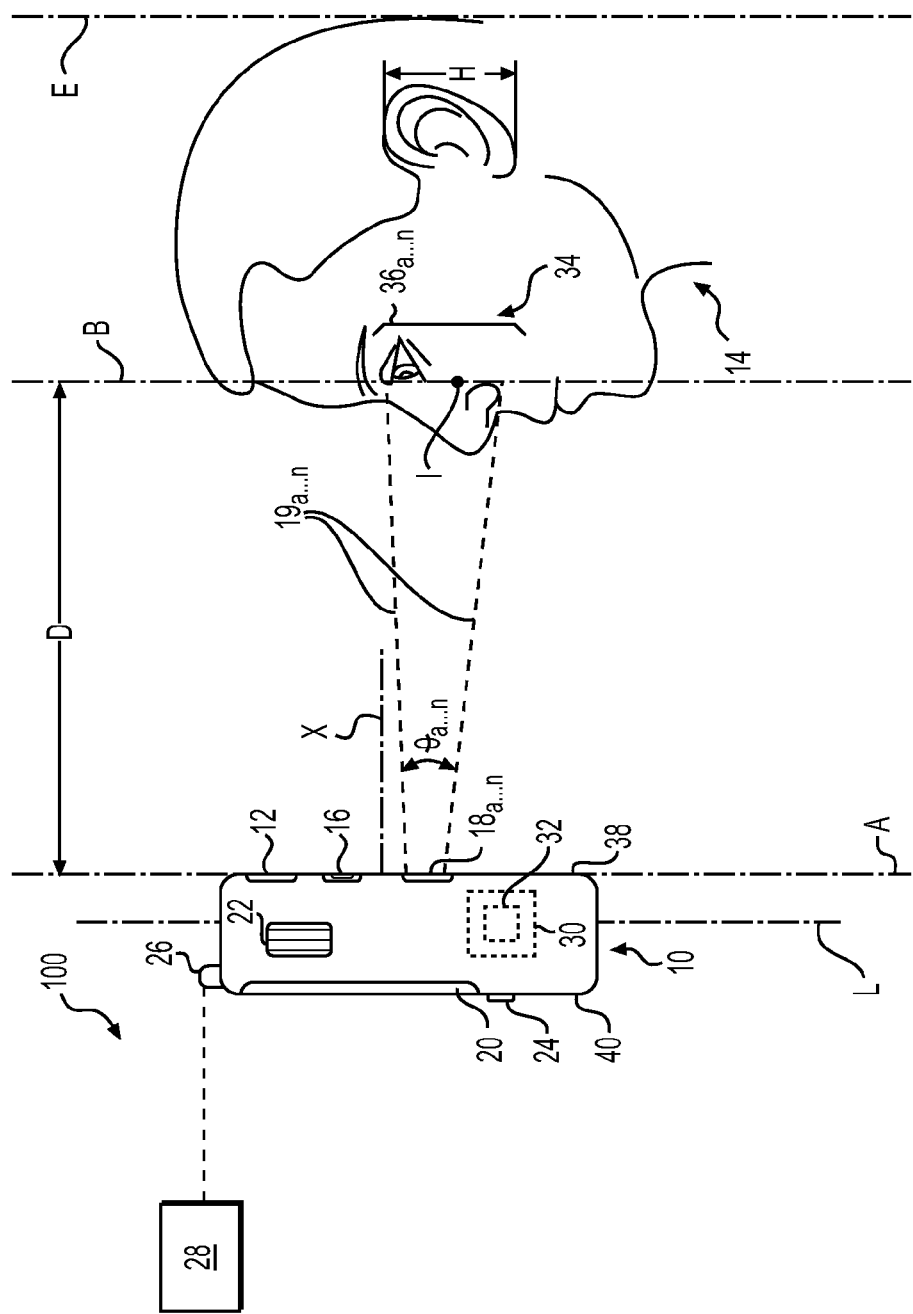
FIG. 1 illustrates a temperature measurement system according to an example embodiment of the present disclosure.

FIG. 1 illustrates an example temperature measurement system 100 of the present disclosure including a temperature measurement device 10. The temperature measurement device 10 of the system 100 may include a first sensor 12 configured to determine that the device 10 is located within a predetermined and/or desired distance range of a patient 14. Such a distance range may be characterized by a distance D, and the distance range and/or the distance D may extend from a plane A substantially defined by the device 10 to a plane B substantially defined by the patient 14. For example, as will be described in greater detail below, such a distance range may extend from the plane A to a plane B substantially defined by at least a portion 34 of the face of the patient 14. In still further examples, such a distance range may extend from the plane A to a plane B substantially defined by any other portion and/or "measurement site" formed by an external surface of the patient's skin, such as the face, forehead, temple, ears (such as the outer or inner ear), eyes, nose, lips, neck, wrist, chin, open mouth, and/or other like skin surfaces. Such measurement sites may also include the oral cavity, rectal cavity, axilla area, ear drum, groin, sub-clavian, and/or other known body cavities or areas. In example embodiments, the plane B may comprise and/or be substantially parallel to a coronal plane of the patient 14. Additionally, the plane B may extend substantially parallel to a spinal axis E of the patient 14.

As shown in FIG. 1, the temperature measurement device 10 may also include an imaging device 16 configured to assist in forming an image of the patient 14, and at least one additional sensor 18a . . . 18n (collectively, "sensors 18") separate from the first sensor 12 and the imaging device 16. In example embodiments, the sensors 18 may be configured to determine respective temperatures of locations 36a . . . 36n (collectively, "locations 36") on the portion 34 of the face and/or any of the other measurement sites described herein. In some embodiments, the sensors 18 may comprise non-contact temperature sensors configured to determine the respective temperatures without contacting the patient 14, the locations 36, and/or other measurement sites. For ease of description, and without limiting the extent of the present disclosure, such temperature determinations will be described herein with respect to the face of the patient 14 unless otherwise specified.

Additionally, the temperature measurement device 10 may include one or more displays 20, signal devices 22, user interfaces 24, and/or communication devices 26. Further, one or more components of the temperature measurement device 10 may be in communication with and/or otherwise connected to a controller 30 of the device 10 and/or memory 32 associated with the controller 30. One or more components of the temperature measurement device 10 may also be in communication with and/or otherwise connected to one or more remote components 28 of the system 100, and such remote components 28 may include one or more controllers, additional temperature measurement devices, servers, computers, databases, displays, hand-held devices, tablet devices, cellular phones, and the like. In such embodiments, the one or more components of the temperature measurement device 10 may communicate with such remote components 28 via the communication device 26.

Whenever possible, like item numbers will be used throughout this disclosure to identify like components of the temperature system 100. Additionally, as will be described herein, the described implementations of the present technology in the temperature measurement device 10 are merely examples. The disclosed technology may be applicable to any other medical device that may use one or more sensors to calculate, estimate, look-up, measure, sense, monitor, and/or otherwise "determine" a temperature of a patient 14. Such a temperature may include a temperature of a measurement site of the patient 14, and such temperatures may comprise surface or skin temperatures of the patient 14 at the measurement site. Additionally, such a temperature may include any internal temperature of the patient 14, such as a sub-skull temperature, a rectal temperature, an oral temperature, an axillary temperature, a "core" temperature, and/or any other like temperature of the patient 14. Additionally, the device 10 and/or one or more sensors thereof may be configured to determine other indicators of patient health such as vaso-dilation, an emerging fever, a diminishing fever, and the like. Such indicators may be determined, for example, based at least in part on one or more of the temperatures determined by the sensors 18. Such medical devices may include, for example, probes, scopes, and/or other like contact-based and/or noncontact-based devices.

The temperature measurement device 10 of example system 100 may comprise, for example, a hand-held device having a first side 38 and a second side 40 opposite the first side 38. Although not shown in FIG. 1, in some embodiments the device 10 may include a handle or other like component configured to assist the user in holding, manipulating, and/or orienting the device 10 relative to the patient 14. Alternatively, as shown in FIG. 1, the device 10 may be substantially rectangular, substantially square, and/or any other known shape. In example embodiments, the thickness (i.e., the distance between the first side and the second side) and/or the length of the device 10 may be minimized so as to improve the ergonomics of the device 10. Although not expressly labeled in FIG. 1, the device 10 may include a one-piece or multi-piece housing and/or other like components, and corners and/or edges of the device 10 may be sufficiently rounded and/or otherwise configured so as not to cause injury to the patient 14 or the user upon contact therewith. Further, the housing and/or other components of the device 10 may be made from any material and/or combinations of materials commonly used in medical and/or examination devices. Such materials may include, for example, plastics, polymers, composites, stainless steel, alloys, and/or any other like materials. Such materials may be suitable for repeated use and/or repeated sanitation. Accordingly, in an example embodiment of the present disclosure, the temperature measurement device 10 and/or its components may be substantially waterproof. One or more waterproof seals may be included and/or otherwise utilized with components of the temperature measurement device 10 to facilitate such repeated sanitation and/or use.

In an example embodiment, the first sensor 12 may comprise a proximity sensor and/or other like device configured to determine a distance between the sensor 12 and one or more objects disposed in the vicinity of the sensor 12 without contacting the object. Such a sensor 12 may also be configured to determine the length, width, height, angular orientation, and/or other dimension or orientation of such objects relative to the sensor 12. Such dimensions may include, for example, a height H of an ear of the patient 14, the height and/or width of a nose of the patient 14, the distance between the eyes of the patient 14, an inner-canthal distance, and/or any other like dimension. Such dimensions may also include, for example, a distance between various locations 36 on the portion 34 of the patient's face or on an additional measurement site. Such dimensions may be used to determine, for example, the age, gender, ethnicity, and/or other characteristics of the patient 14.

In example embodiments, the first sensor 12 may be configured to determine whether and/or when the first sensor 12 (and, consequently, the temperature measurement device 10) is within a desired distance range of the object. Such a distance range may correspond to, for example, a field of view of the first sensor 12, and as noted above, an example distance range may be characterized by the distance D illustrated in FIG. 1. Such proximity sensors may include, for example, an inductive sensor, a magnetic sensor, an infrared sensor, a capacitive photoelectric sensor, a sonic distance sensor, and/or any other like proximity sensor known in the art. In such embodiments, the first sensor 12 may emit an electromagnetic field or beam of electromagnetic (such as infrared) radiation. Such a field or beam may impinge upon the object and at least a portion of the field of beam may return to the first sensor 12. In such embodiments, the first sensor 12 may determine a change in the field or return beam, and may determine the distance D between the first sensor 12 and the object based on the determined change. In such embodiments, the first sensor 12 may comprise a plurality of components including, for example, an emitter, a receiver, and/or other like sensing devices. Such an example first sensor 12 is further illustrated in FIG. 3.

Figure 3:
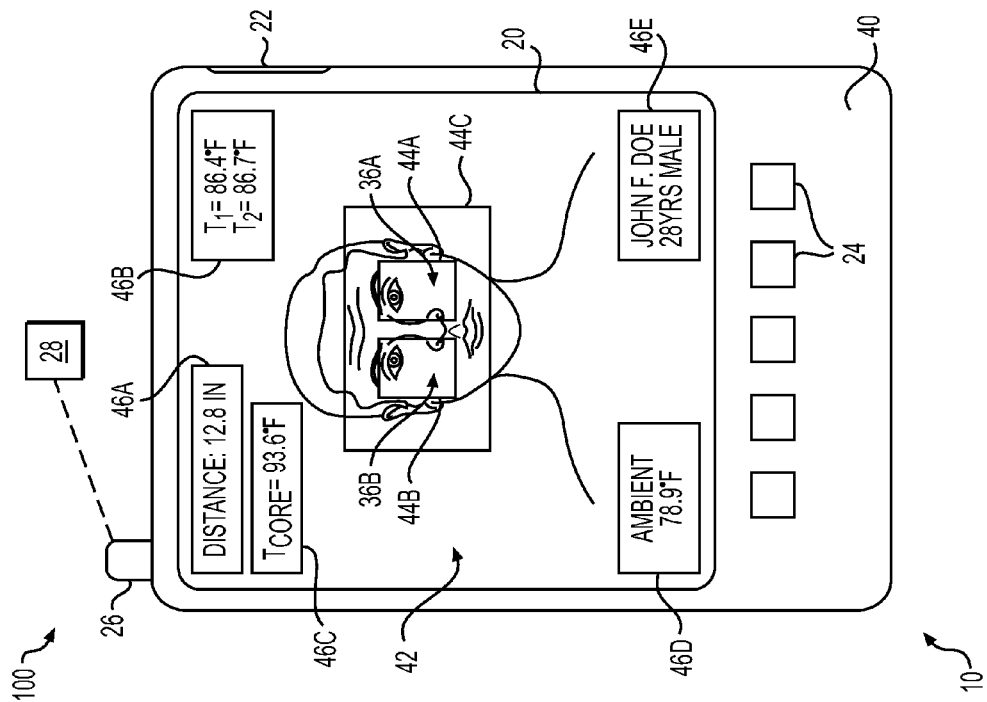
FIG. 3 illustrates a second view of the temperature measurement device shown in FIG. 2.

As shown in at least FIGS. 1 and 3, in an example embodiment the first sensor 12 may be disposed such that at least one of an emitter, receiver, and/or other component of the first sensor 12 is disposed substantially coplanar with the first side 38. In such embodiments, the first side 38 may be substantially coplanar with the plane A, and at least a portion of the first sensor 12 may also be substantially coplanar with the plane A. As shown in FIG. 1, the distance range may extend from the plane A to the plane B. As noted above, the plane B may be substantially defined by the portion 34 of the face of the patient 14, and the portion 34 of the face may comprise an inner-canthal region, a sinus region, a temple region, a cheek region, and/or other region of the face. As shown in at least FIG. 1, portion 34 of the face defining the inner-canthal region may comprise a region of the face including the tear ducts. For example, such a region of the face may extend from approximately the nose of the patient 14 to at least a portion of each eye (such as a corner of each eye), and may include at least a portion of the sinus region and/or upper cheek. The locations 36 on the portion 34 may comprise particular points, areas, and/or other identifiable locations within the specified region. In further example embodiments, however, the plane B may be substantially defined by any of the alternative measurement sites described herein. In example embodiments, the distance range described herein with respect to the first sensor 12 may be less than approximately 24 inches. For example, the distance range characterized by the distance D may be between approximately 0.01 inches and approximately 24 inches, or alternatively between approximately 6 inches and approximately 14 inches. It is understood that the first sensor may be tuned, focused, and/or otherwise configured to employ a distance range that is not overly intrusive to the patient 14 while the device 10 is being used to determine a temperature of the patient 14. Further, minimizing the distance range may result in an increase in the accuracy of the patient temperature determined by the device 10.

The imaging device 16 may comprise, for example, one or more digital cameras, infrared sensors, and/or other like devices configured to assist in generating an image of the patient 14. For example, the imaging device 16 may comprise a digital camera operably connected to the controller 30 and/or the display 20, and the imaging device 16 may be configured to capture an image of the measurement site and/or other portions of the patient 14. Alternatively or in addition, the imaging device 16 may be configured to collect thermal, infrared, and/or other radiation emitted by the patient 14, and to assist in forming a thermal image of the patient 14 using and/or based on the collected radiation. In such example embodiments, the imaging device 16 may be configured to send information and/or signals to the controller 30 and/or the display 20, and the display 20 may display an image of the patient 14 using and/or based on such signals.

Figure 2:
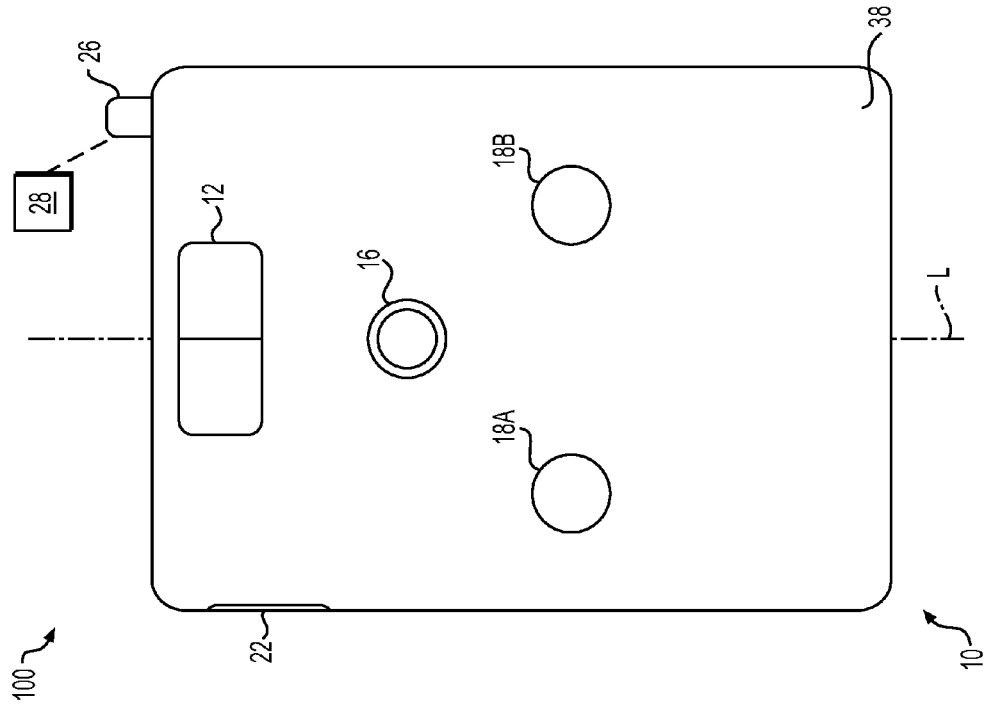
FIG. 2 illustrates a first view of an example temperature measurement device associated with the system shown in FIG. 1.

In example embodiments, the controller 30 may include components such as an image processor and/or image processing software configured to receive information and/or signals from the imaging device 16. The image processor may be configured to assist in forming the image of the patient 14 based on such inputs. For example, in embodiments in which the imaging device 16 comprises a digital camera, the image processor may receive information and/or signals from the imaging device 16, and may assist in forming a visual image of the patient 14 based on such inputs. As shown in FIG. 2, such a visual image 42 may be illustrated on the display 20 of the temperature measurement device 10.

Alternatively, in embodiments in which the imaging device 16 is configured to collect thermal, infrared, and/or other radiation emitted by the patient, the image processor may receive information and/or signals from the imaging device 16 indicative of such collected radiation. In such embodiments, the image processor may assist in forming a thermal image (not shown) of the patient 14 based on such inputs. Similar to the visual image 42 described above, the thermal image may be illustrated on the display 20, and such a thermal image may comprise a two or three-dimensional image, temperature gradient, and/or temperature profile of the patient 14.

In example embodiments, the temperature measurement device 10 may be configured to determine one or more physical attributes of the patient 14, and the controller 30 may be configured to automatically select an operating mode of the device 10 based on the determined attribute. For example, the imaging device 16, the first sensor 12, and/or one or more of the images described herein may be used by the image processor and/or other components of the controller 30 to determine a distance between a first location 36a on the portion 34 of the face of the patient 14 and a second location 36b on the portion 34, a distance between at least one of the first and second locations 36a, 36b and a third location 36c on the face of the patient 14, a length, width, height, and/or other dimension related to an ear (such as the height H shown in FIG. 1), nose, eye, cheek, chin, and/or other body part of the patient 14, and/or other like attributes. One or more such attributes may be used to determine, for example, the age, gender, ethnicity, and/or other characteristics of the patient 14, and the controller 30 may automatically select one or more temperature algorithms, lookup tables, neural networks, and/or other like temperature determination components or protocols for use based on such a determination.

For example, upon initial screening of the patient 14, the imaging device 16 may assist in generating a digital image 42 of the patient 14. Additionally, the first sensor 12 may determine one or more distances associated with the patient 14, such as a distance from the center of the pupil of the left eye of the patient 14 to the center of the pupil of the right eye of the patient 14. Alternatively, the distance from the corner of the left eye to the corner of the right eye may be determined. In still further embodiments, the height H (e.g., top to bottom) of the patient's ear may be determined. The imaging device 16 and/or the first sensor 12 may send corresponding information and/or signals to the image processor and/or other components of the controller 30, and such components may determine an age range of the patient 14 based on such inputs. For instance, based on one or more such inputs, the components may determine whether the patient 14 is an infant, an adolescent youth, or an adult. Upon making such a determination, the controller 30 may select a corresponding operating mode of the device 10 based on the determination. In such embodiments, selecting such an operating mode may comprise selecting a set of temperature determination algorithms for use in core temperature determinations associated with the patient 14. It is also understood that the controller 30 may select such an operating mode based at least partially on the determined distance and/or other attributes of the patient 14 without making further determinations as to, for example, the age, gender, ethnicity, and/or other characteristics of the patient 14. Additionally, one or more of the determined attributes and/or characteristics may be illustrated on the display 20 separately and/or as part of the image 42. Further, as will be described in more detail below, the controller 30 may select an output type (e.g., providing a temperature based on an axillary reference for pediatric patients, etc.) based at least in part on the determined distance and/or any of the above characteristics of the patient 14.

The sensors 18 may comprise any devices configured to sense one or more vital signs or physical characteristics of a patient such as, for example, temperature, blood pressure, blood oxygen saturation (hereinafter "$SpO_2$"), heart rate, and the like. In an example embodiment, at least one of the sensors 18 may comprise a temperature sensor, such as a thermopile, thermocouple, and/or thermistor, configured to determine a temperature associated with the patient 14. For example, each of the sensors 18 may be configured to determine a temperature of respective locations 36 on the portion 34 of the face of the patient 14. Alternatively, each of the sensors 18 may be configured to determine a temperature of other respective measurement sites of the patient 14. It is understood that in some example embodiments, determining a temperature of the patient 14 with the temperature measurement device 10 may include contacting one or more patient measurement sites with the temperature measurement device 10 and/or with at least a portion of one or more of the sensors 18. Alternatively, in other example embodiments, a temperature of the patient 14, such as a core temperature of the patient 14, may be determined without contacting the measurement site and/or other portions of the patient 14 with the device 10 or with the sensors 18 associated therewith. For the duration of the disclosure, such noncontact temperature determination methods will be described in greater detail unless otherwise specified.

In example embodiments, one or more of the sensors 18 may comprise an infrared temperature sensor such as, for example, a thermopile and/or other like infrared-based temperature sensing devices. In still further embodiments, one or more of the sensors 18 may comprise an array of pixels and/or other like sensing elements configured to determine a temperature of the various measurement sites described herein. Such sensors 18 may be configured to convert thermal energy into electrical energy, and may comprise two or more thermocouples connected in series or in parallel. Such components may be configured to generate an output voltage proportional to a local temperature difference and/or temperature gradient. In an example embodiment in which one or more of the sensors 18 comprises at least one thermopile, the temperature measurement device 10 may comprise, for example, an infrared thermometer. In such embodiments, the sensors 18 may be configured to receive and/or emit radiation, such as thermal and/or infrared radiation. For example, the sensors 18 may be configured to sense, detect, collect, and/or otherwise receive radiation emitted by the measurement site, such as, by respective locations 36 on the portion 34 of the face of the patient 14. In such embodiments, the sensors 18 may be configured to collect the radiation, and to send a signal to the controller 30 indicative of the collected radiation. For example, a first sensor 18a may be configured to collect radiation from a first location 36a, and a second sensor 18b may be configured to collect radiation from a second location 36b. In this way, the first sensor 18a may be configured to determine a temperature of the first location 18a while the second sensor 18b may be configured to determine a temperature of the second location 36b. The controller 30 may utilize the information received from the sensors 18 for any number of known functions. For example, the controller 30 may be configured to determine a core temperature of the patient 14 based on such information and/or on one or more additional inputs.

As shown in at least FIGS. 1 and 3, one or more of the sensors 18 may be embedded substantially within and/or formed integrally with the device 10, and at least a portion of at least one of the sensors 18 may be disposed substantially coplanar with the first side 38 and/or with the plane A. Additionally, each of the sensors 18 may have a respective field of view $19a \ldots 19n$ (collectively referred to as "fields of view 19") that is characterized by a respective angle $\Theta_a \ldots \Theta_n$ (collectively referred to as "angles $\Theta$"). For example, such fields of view 19 may be substantially conical, substantially cylindrical, and/or any other three-dimensional shape, and may extend from each respective sensor $18a \ldots 18n$ to the measurement site. Such fields of view 19 may be characterized by any desirable angles $\Theta$ commonly associated with the sensors 18. For example, such fields of view 19 may be characterized by angles $\Theta$ less than approximately 20 degrees, and in some embodiments, by angles $\Theta$ between approximately 5 degrees and approximately 15 degrees. In such embodiments, the fields of view 19 may define the range and/or area of sensitivity for the corresponding sensors 18. For example, objects disposed within the field of view 19a of the first sensor 18a may be detected and/or sensed by the sensor 18a, and the sensor 18a may not be capable of sensing objects disposed outside of the field of view 19a. Similarly, objects disposed within the field of view 19b of the second sensor 18b may be detected and/or sensed by the second sensor 18b, and the sensor 18b may not be capable of sensing objects disposed outside of the field of view 19b.

Additionally, such fields of view 19 may have any length commensurate with the noncontact sensors 18 described herein, and the length of such fields of view 19 may extend to and/or otherwise be characterized by the distance D illustrated in at least FIGS. 1 and 4. In such embodiments, objects located at a distance less than or substantially equal to the distance D (i.e., within the fields of view 19a, 19b of the sensors 18a, 18b) may be detected and/or sensed by the sensors 18a, 18b, while objects located at a distance greater than the distance D (i.e., outside of the fields of view 19a, 19b of the sensors 18a, 18b) may not be detected and/or sensed by the sensors 18a, 18b. Accordingly, in example embodiments the first sensor 12 may be configured to determine that at least one of the first location 36a is within the field of view 19a of the sensor 18a and the second location 36b is within the field of view 19b of the sensor 18b. In example embodiments, determining that the temperature measurement device 10 is located within a desired distance range of the portion 34 of the face of the patient 14 may include determining at least one of the first location 36a is within the field of view 19a of the sensor 18a and the second location 36b is within the field of view 19b of the sensor 18b. In such embodiments, the first sensor 12 may be tuned such that the field of view thereof (i.e., the desired distance range characterized by the distance D) corresponds to and/or otherwise has a length substantially equal to the lengths of the fields of view 19 of the sensors 18. It is understood that in further embodiments, more than one distance may be determined by the first sensor 12 in order to determine whether, for example, the temperature measurement device 10 is located within a desired distance range of the portion 34. In such embodiments, the first sensor 12 may determine a respective distance between the locations 36a, 36b and each of the respective sensors 18a, 18b to whether at least one of the first location 36a is within the field of view 19a of the sensor 18a and the second location 36b is within the field of view 19b of the sensor 18b. In still further embodiments, the device 10 may include two or more first sensors 12 to facilitate determining multiple distances. In such embodiments, one sensor 12 may be configured to determine a distance between the location 36a and the sensor 18a, while an additional sensor 12 may be configured to determine a distance between the location 36b and the sensor 18b.

The first sensor 12 may provide one or more signals to the controller 30 indicating that at least one of the locations 36a, 36b is within a corresponding field of view 19a, 19b of a respective sensor 18a, 18b, and the controller 30 may assist in providing one or more indications 44a, 44b, 44c (collectively referred to herein as "indications 44") to the user of the device in response to such signals from the first sensor 12. Such indications 44 may include audible, visible, and/or tactile indications, and example indications 44 are shown in at least FIG. 2 as being illustrated in the image 42 of the patient 14 shown on the display 20. For instance, a first indication 44a may comprise a visible box, circle, window, and/or other marker overlaying the first location 36a in the image 42 of the patient 14, and a second indication 44b may comprise a visible box, circle, window, and/or other marker overlaying the second location 36b in the image 42. In such embodiments, the first indication 44a may be indicative of the first location 36a being disposed within the field of view 19a of the first sensor 18a and the second indication 44b may be indicative of the second location 36b being disposed within the field of view 19b of the second sensor 18b. Example embodiments may also include additional indications 44c comprising one or more visible boxes, circles, windows, and/or other markers generally overlaying at least part of the face of the patient 14 in the image 42. In still further embodiments, such indications 44 may include text, symbols, graphics, and/or other like notations in the image 42 indicating that the device 10 is oriented and/or located such that the locations 36 are disposed within the respective fields of view 19. In example embodiments, such indications 44 may not be shown in the image 42 until the device 10 is oriented and/or located as described above.

It is understood that such indications 44 may be useful in prompting input from a user of the device 10. For example, upon hearing, feeling, and/or viewing such indications 44, the user may provide one or more inputs via the display 20 and/or one or more of the user interfaces 24. For example, upon viewing one or more of the indications 44a, 44b indicative of the locations 36a, 36b being disposed within the fields of view 19a, 19b of the respective sensors 18a, 18b, a user of the temperature measurement device 10 may actuate one of the user interfaces 24 to activate one or more of the sensors 18. Alternatively, in exemplary embodiments in which the display 20 comprises a touch screen or other like device configured to accept input, the user may touch and/or otherwise interact with the display 20 to activate one or more of the sensors 18. In any of the embodiments described herein, the temperature measurement device 10 may determine the temperature of the first location 36a, the temperature of the second location 36b, and/or the core temperature of the patient 14 in response to input received by the user. Alternatively, the temperature measurement device 10 may determine one or more of the above temperatures automatically (i.e., without receiving input from the user) upon determining that the device 10 is located within the distance range of the portion 34 of the face. The temperature measurement device 10 may also determine one or more of the above temperatures automatically (i.e., without receiving input from the user) upon determining that one or more of the locations 36 is disposed within or more of the fields of view 19 described above. In example embodiments, the controller 30, image processor, and/or the image processing software associated therewith may automatically activate one or more of the sensors 18 to determine respective temperatures in response to, for example, determining that the device 10 is located within the distance range of the portion 34 of the face. In still further embodiments, the remote component 28 of the system 100 may employ such image processing software and may be operable to automatically activate one or more of the sensors 18 to determine respective temperatures in a similar fashion.

It is also understood that such indications 44 may be indicative of one or more additional alignment parameters associated with the device 10 and/or one or more of the sensors 12, 18, and such alignment parameters are illustrated in at least FIGS. 1 and 4-6. For example, such alignment parameters may include the distance range described above with respect to the distance D. Additionally, the first sensor 12 may comprise one or more gyroscopes, accelerometers, and/or other components configured to determine an angular position of the temperature measurement device 10 relative to another object. For example, the sensor 12 may be configured to determine the magnitude of one or more angles formed between the temperature measurement device 10 and the plane B substantially defined by the portion 34 of the face and/or other measurement sites of the patient 14. In example embodiments, such angles may be formed between the plane B and at least one of the sensor 12, the plane A, and the first surface 38, and any of the angles described herein may comprise additional alignment parameters determined by the sensor 12.

With respect to the embodiment shown in the top view of FIG. 5, such angles $\alpha_a$-$\alpha_c$ may be formed by, for example, rotating and/or otherwise moving the temperature measurement device 10 from side to side about an axis C. In such embodiments, the axis C may be substantially parallel to the spinal axis E, and may extend along and/or within the plane B. In example embodiments, the sensors 18 may have a preferred angular alignment range F within which the accuracy of temperature determinations made by the sensors 18 may be optimized. Such a preferred angular alignment range F may comprise an additional alignment parameter of the present disclosure, and the first sensor 12 may be configured to determine when the sensors 18, and the temperature measurement device 10 generally, are located within the preferred angular alignment range F relative to the portion 34 of the face and/or relative to respective locations 36 on the portion 34. Additionally, one or more of the indications 44 described above may be provided to the user of the device 10 in response to determining that the temperature measurement device 10 is located within the preferred angular alignment range F.

Such angles $\alpha_a$-$\alpha_c$ may be formed between the plane B and a normal line extending substantially perpendicularly from the plane A, the first side 38, and/or the sensor 12 through the axis C. When, for example, the sensor 12 and/or the temperature measurement device 10 is disposed substantially parallel to the plane B, an angle $\alpha_a$ equal to approximately 90 degrees may be formed between the plane B and the normal line. Alternatively, rotating the temperature measurement device 10 about the axis C, such as by rotating the temperature measurement device 10 about the face of the patient 14, may increase (angle $\alpha_c$) or decrease (angle $\alpha_b$) the magnitude of the angle $\alpha$ formed between the normal line and the plane B. In example embodiments, the sensors 18 may determine temperatures of the respective locations 36 when the temperature measurement device 10 is disposed substantially parallel to the portion 34 of the face (i.e., when the angle $\alpha_a$ formed between the plane B and the normal line is equal to approximately 90 degrees). It is understood, however, that temperature determinations made by the sensors 18 may also have an acceptable accuracy for some applications when the angle $\alpha$ is within the preferred angular alignment range F. Such a preferred angular alignment range F for the angle $\alpha$ may be between approximately 75 degrees and approximately 105 degrees. The accuracy of such temperature determinations may be considered "acceptable" when the temperature measured using the sensors 18 is within approximately 10 percent of a corresponding temperature measured using one or more additional sensors (not shown) via patient contact.

Figure 6:
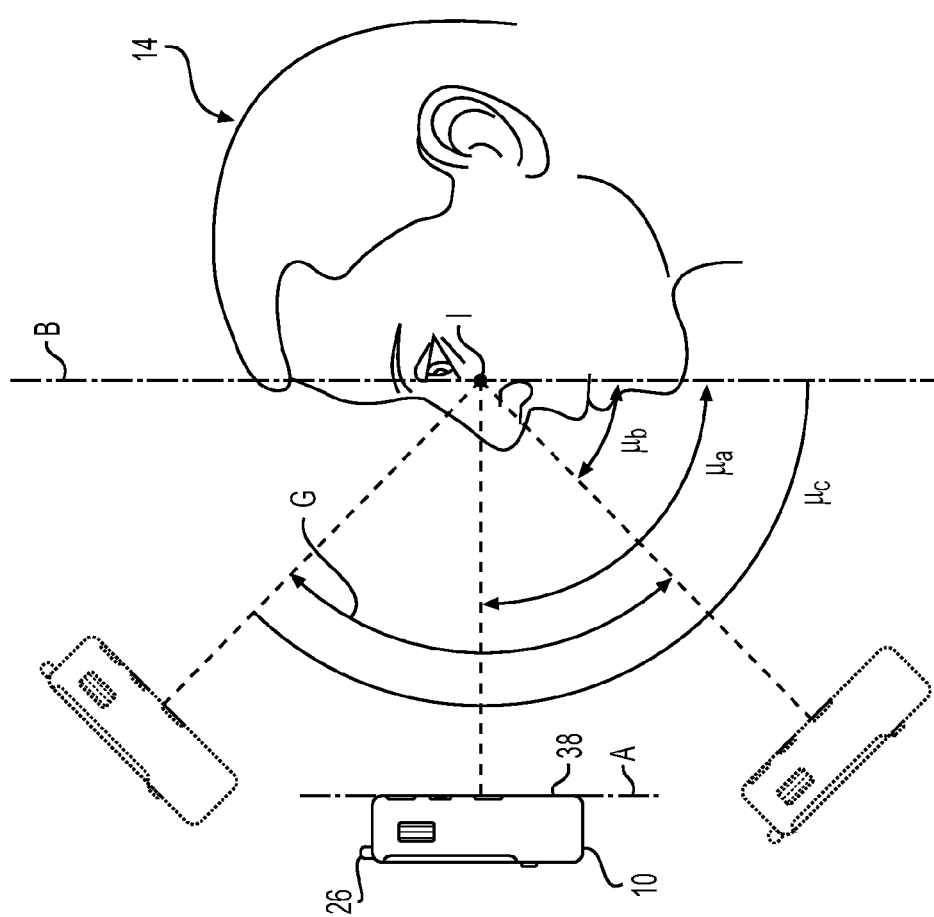
FIG. 6 is another schematic diagram illustrating various positions of an example temperature measurement device relative to a plane.

As shown in the side view of FIG. 6, rotating the temperature measurement device 10 about an axis I may result in angles $\mu_a$-$\mu_c$ formed between the plane B and the normal line extending substantially perpendicularly from the first side 38, plane A, and/or the first sensor 12 through the axis I. In such embodiments, the axis I may extend substantially perpendicular to the axis C described above, and may extend along and/or substantially within the plane B. When the sensor 12 and/or the temperature measurement device 10 is disposed substantially parallel to the plane B, an angle $\mu_a$ equal to approximately 90 degrees may be formed between the plane B and the normal line. Alternatively, rotating the temperature measurement device 10 about the axis I, such as by rotating the temperature measurement device 10 from the forehead to the chin of the patient 14, may increase (angle $\mu_c$) or decrease (angle $\mu_b$) the magnitude of the angle $\mu$ formed between the normal line and the plane B. In additional example embodiments, the angle $\mu$ described herein may comprise a further alignment parameter associated with the temperature measurement device 10.

In example embodiments, the sensors 18 may determine respective temperatures of the locations 36 when the temperature measurement device 10 is disposed substantially parallel to the portion 34 (i.e., when the angle $\mu_a$ formed between the plane B and the normal line is equal to approximately 90 degrees). It is understood, however, that temperature determinations made by the sensors 18 may also have an acceptable accuracy for some applications when the angle $\mu$ is within a preferred angular alignment range G. Such a preferred angular alignment range G for the angle $\mu$ may be between approximately 75 degrees and approximately 105 degrees. As described above, the accuracy of such temperature determinations may be considered "acceptable" when the temperature measured using the sensors 18 is within approximately 10 percent of a corresponding temperature measured using one or more additional sensors (not shown) via patient contact.

The temperature measurement device 10 may additionally include at least one window, lens, filter, and/or other like optical component (not shown) positioned proximate one or more of the sensors 12, 18, and/or the imaging device 16. For example, such an optical component may be disposed substantially flush and/or coplanar with the first side 38 of the device 10. Such optical components may be configured to assist in, for example, focusing, directing, and/or otherwise transmitting radiation to the sensors 12, 18, and/or the imaging device 16 for collection. In additional example embodiments, such optical components may assist in focusing, directing, and/or otherwise transmitting radiation emitted by one or more of sensors 12, 18. Such optical components may also assist in protecting the thermopile, thermocouple, thermistor, photo sensors, and/or other components of the sensors 12, 18, and/or the imaging device 16 during use of the temperature measurement device 10, and may assist in forming a substantially fluid-tight compartment (not shown) within the device 10 to protect such components from contact with bodily fluids, cleaning solutions, and/or other liquids. It is understood that such optical components may be substantially transparent to assist in the transmission of infrared and/or other types of radiation. In example embodiments, the optical components may comprise one or more convergent, collimating, and/or divergent lenses. Additionally, in such embodiments at least a component of at least one of the sensors 12, 18 and/or at least a component of the controller 30 may be disposed within the substantially fluid-tight compartment.

In further example embodiments, the temperature measurement device 10 may include one or more actuation devices (not shown) associated with one or more of the sensors 12, 18, and/or the imaging device 16. Such actuation devices may be operably connected to the controller 30 and may be configured to move the sensors 12, 18, and/or the imaging device 16 relative to the temperature measurement device 10. For example, in the embodiment shown in FIG. 1 such actuation devices may be configured to pivot the sensors 12, 18, and/or the imaging device 16 relative to the first side 38 and/or any other portion of the temperature measurement device 10. In such an example embodiment, the one or more actuation devices may be configured to pivot the sensors 12, 18, and/or the imaging device 16 about a longitudinal axis L of the temperature measurement device 10 extending substantially parallel to the plane A from a top of the device 10 to a bottom thereof. In further example embodiments, such actuation devices may be configured to move the sensors 12, 18, and/or the imaging device 16 longitudinally (i.e., along the longitudinal axis L) and/or laterally (i.e., transverse to the longitudinal axis L) along the first side 38 of the temperature measurement device 10.

The example actuation devices described above may comprise any electric motor, servo motor, and/or other known device configured to assist in moving one or more components of the sensors 12, 18, and/or the imaging device 16 relative to the device 10. Accordingly, it may be possible to form any of the angles $\alpha$, $\mu$ described herein with respect to FIGS. 5 and 6 through activation of one or more such actuation devices while maintaining the position of the temperature measurement device 10 substantially stationary with respect to the plane B and/or the patient 14. Additionally and/or alternatively, in further embodiments at least one of the sensors 12, 18 and/or the imaging device may be positioned at an angle relative to, for example, the first side 38. For example, at least one of the sensors 18 may be angled toward an axis X extending substantially perpendicular from the longitudinal axis L and/or the first side 38. Such an example axis X is shown in FIGS. 1 and 4. In such examples, at least one of the sensors 18 may be angled inward and/or otherwise aimed toward the eyes and/or the inner-canthal region of the face of the patient 14. Additionally, in any of the examples described herein, one or more of the sensors 12, 18 and/or the imaging device 16 may be moveable in order to maintain focus on the respective locations 36 as, for example, the patient 14 and/or the temperature measurement device 10 is moved. One or more of the sensors 12, 18 and/or the imaging device 16 may also be moveable in response to and/or based on the determination of one or more physical attributes of the patient 14. Such physical attributes will be described in greater detail below.

As discussed above, and as illustrated in at least FIGS. 1 and 2, the temperature measurement device 10 may include one or more displays 20. An example display 20 may be operably connected to the controller 30 and/or to the image processor thereof. The display 20 may comprise, for example, a liquid crystal display (LCD) screen, a light emitting diode (LED) display, a digital read-out, an interactive touch-screen, and/or any other like components configured to communicate information to the user or to control the temperature measurement device 10. In addition to the various indications 44 described herein, as shown in FIG. 2, such displays 20 may be configured to indicate, for example, one or more distances 46a, such as the distance D associated with the distance range and/or fields of view 19 described herein. Such displays 20 may also be configured to indicate temperatures 46b determined by the sensors 18, and one or more temperatures 46c, such as a core temperature of the patient 14, determined based on signals received from one or more of the sensors 18. Although FIG. 2 illustrates the temperatures 46b, 46c being shown in separate respective windows on the display 20, in further example embodiments, one or more of the temperatures 46b, 46c, such as the temperatures determined by the sensors 18, may be shown on the display 20 within corresponding respective indications 44a, 44b, or elsewhere on a corresponding location 36 of the face. Additionally, such displays 20 may be configured to indicate an ambient temperature 46d associated with the environment in which the device 10 is being used, the name, age, gender, and/or any other information 46e that may be useful during operation of the temperature measurement device 10. For example, the display 20 may also be configured to communicate information indicative of the angles $\alpha$, $\mu$, fields of view 19, and/or other alignment parameters described herein. The display 20 may also be configured to communicate information indicative of additional physical characteristics of the patient 14 including but not limited to disease state, injury, and emotional state. The display 20 may be configured to communicate such information substantially simultaneously and/or substantially continuously depending on the mode of operation of the temperature measurement device 10.

With continued reference to FIGS. 1 and 2, example signal devices 22 of the temperature measurement device 10 may include, for example, one or more lights, LEDs, speakers, and/or other like devices configured to emit an audible and/or visible alarm or signal in response to a command or signal from the controller 30. Such an alarm or other signal may be initiated by, for example, the controller 30 when a temperature determined by the temperature measurement device 10 meets or exceeds a threshold temperature. In additional example embodiments, such an alarm or signal may be initiated during a substantially continuous temperature determination operation where the rate of patient temperature change meets or exceeds a predetermined temperature change rate threshold.

In further example embodiments, such an alarm or signal may be initiated and/or otherwise communicated to a user of the temperature measurement device 10 based on one or more of the alignment parameters described herein. For example, the signal device 22 may be configured to output information indicative of one or more such alignment parameters to assist the user in positioning the temperature measurement device 10 and/or the sensors 18 relative to the patient 14. In example embodiments, the signal device 22 may output an audible alarm, signal, and/or other indication indicating that the temperature measurement device 10 and/or the sensors 18 are disposed outside of the angular alignment ranges F, G and/or the fields of view 19 described herein. Alternatively, the signal device 22 may be configured to output an audible alarm, signal, and/or other indication indicating when the temperature measurement device 10 and/or the sensors 18 have been positioned within the angular alignment ranges F, G and/or the fields of view 19 described herein.

In each of the example embodiments described herein, one or more of the signal device 22 and the display 20 may be configured to request and/or direct movement of the patient 14 relative to the temperature measurement device 10, or vice versa. In such embodiments, for example, the signal device 22 and/or the display 20 may output one or more audible and/or visual signals or requests informing the user where to position the patient 14 or the device 10. Such requests may comprise, for example, one or more visual alignment beams, visual images, and/or audible communications/instructions indicating a desired movement of the device 10 relative to a substantially stationary patient 14. In still further embodiments, such requests may comprise visual instructions including one or more of the indications 44 described above.

The one or more user interfaces 24 of the temperature measurement device 10 may be configured to assist in initiating, performing, and/or controlling one or more functions of the temperature measurement device 10. For example, the user interfaces 24 may comprise any combination of switches, buttons, levers, knobs, dials, keys, and/or other like components configured to activate, deactivate, manipulate, and/or otherwise control components of the temperature measurement device 10. Such user interfaces 24 may, for example, assist the user in toggling through and/or selecting one or more modes of operation of the temperature measurement device 10, enabling and/or disabling one or more sensors 12, 18, imaging devices 16, alarms, and/or signal devices 22 associated with the device 10, initiating a single substantially instantaneous temperature determination, initiating a substantially continuous and/or repeating temperature determination, and/or other like modes, functions, or operations. Accordingly, one or more user interfaces 24 may be operably connected to at least one of the sensors 12, 18, the imaging device 16, the display, 20, and/or other components of the temperature measurement device 10. In an example embodiment, at least one of the user interfaces 24 may be embedded substantially within and/or otherwise formed integrally with the device 10 and/or a housing thereof. Additionally, in embodiments in which the display 20 comprises a touch screen, one or more of the user interfaces 24 may be omitted.

The communication device 26 of the temperature measurement device 10 may include one or more transmitters, receivers, transceivers and/or other like communication components configured to send information to and/or receive information from the remote component 28. In such example embodiments, the temperature measurement device 10 may be configured to send and/or receive any of the information described herein with regard to the display 20, sensors 12, 18, imaging device 16, and/or other components of the temperature measurement device 10 via such communication devices 26. In such embodiments, a communication device 26 of the temperature measurement device 10 may be configured to send and/or receive such information to the remote component 28 of the system 100 wirelessly via BLUETOOTH®, WIFI®, cellular networks, internet networks, or other like means. Such a communication device 26 may be disposed at any convenient location on the temperature measurement device 10, and in additional embodiments, such a communication device 26 may be disposed partially and/or completely internal to the temperature measurement device 10. Such remote components 28 may be disposed at a different location in the same examination room as the device 10, in a different examination room and/or other location within the same healthcare facility as the device 10, or in an entirely different healthcare facility than the device 10. Accordingly, the communication device 26 may facilitate communication between a local temperature measurement device 10 and a remote component 28 via any of the means described above depending on the relative locations of the device 10 and the remote component 28.

The controller 30 may be operably connected to the user interfaces 24, display 20, sensors 12, 18, imaging device 16, communication device 26, and/or other components of the temperature measurement device 10, and the controller 30 may be configured to control the operation of such components. In an example embodiment, the controller 30 may be configured to receive signals, information, measurements, and/or other data from the sensors 12, 18 and/or the imaging device 16, and to determine a temperature value indicative of a core temperature of the patient 14 based on the information received. The controller 30 may also be configured to execute one or more commands and/or control programs. In addition to the image processor described above, the controller 30 may comprise memory 32, additional processors, and/or other known controller components to facilitate the functionality described herein. In an example embodiment, the controller 30 may be disposed within, for example, the housing of the temperature measurement device 10. In such an embodiment, the housing may form one or more substantially water-tight and/or substantially hermetically sealed compartments for storing the various components of the controller 30.

The example temperature measurement system 100 described herein may be utilized by physicians, nurses, health care professionals, and/or other users in a variety of different environments. For example, the temperature measurement device 10 may be employed in any of a number of examination facilities to determine one or more temperatures associated with a patient 14 such as, for example, an estimated core temperature of the patient 14. Such an estimated core temperature may be utilized by the health care professional to assist in treating the patient 14, and may have a variety of uses that are well known in the medical field.

Figure 7:
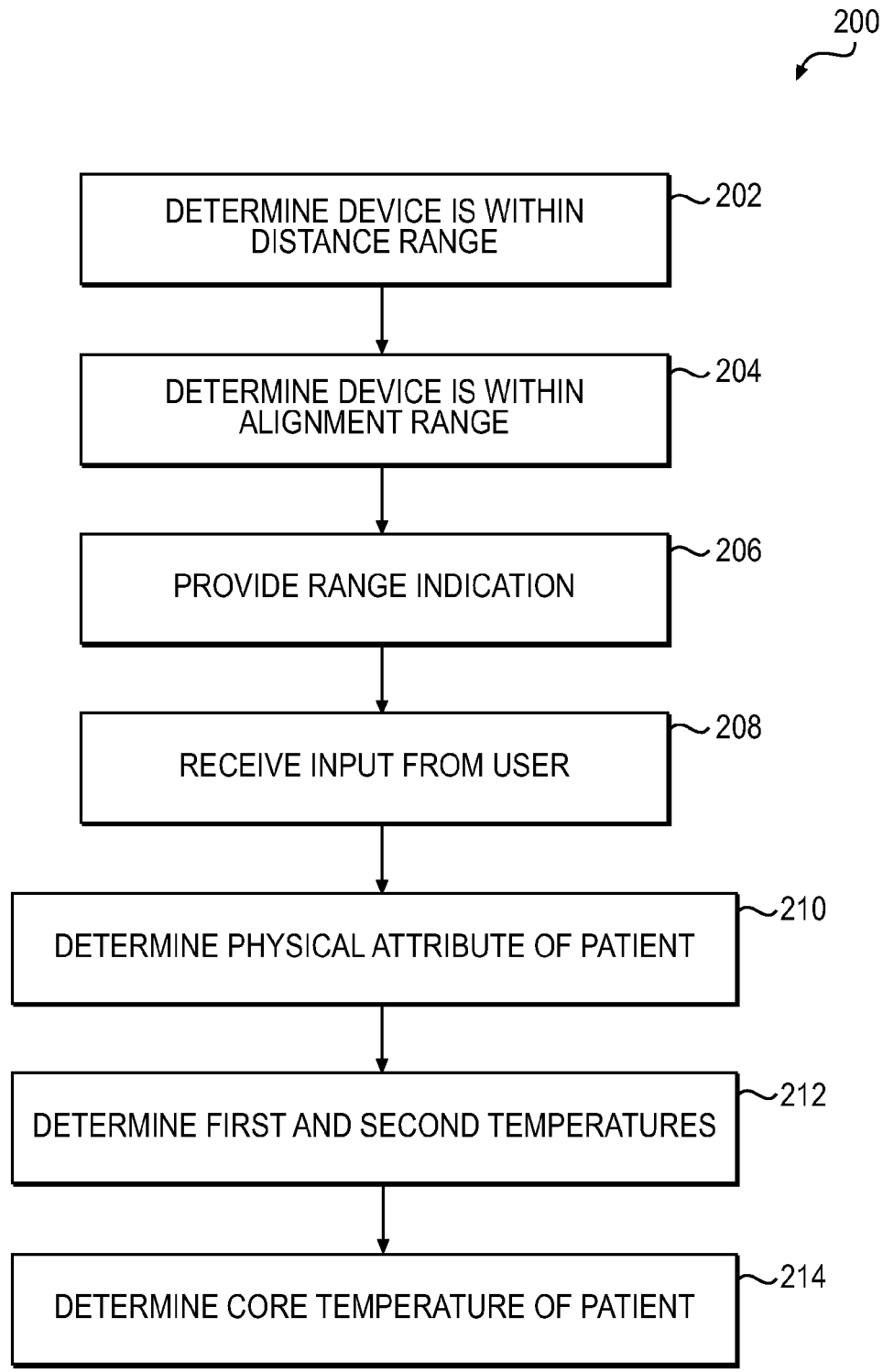
FIG. 7 illustrates a flowchart outlining an example method of use associated with the present disclosure.

In example embodiments, the temperature measurement devices 10 disclosed herein may be configured to determine patient temperature and/or other physical characteristics of the patient 14 using one or more contact-based and/or non-contact-based methods of patient evaluation. For ease of description, a noncontact-based method of temperature determination will be described with respect to the flowchart 200 shown in FIG. 7.

In an example method of determining a temperature of a patient 14, the controller 30 and/or the first sensor 12 of the temperature measurement device 10 may, at step: 202 determine whether the device 10 is located within the distance range described above with respect to the portion 34 of the face of the patient 14. As shown in at least FIG. 1, such a distance range may be characterized by the distance D extending from the plane B substantially defined by the portion 34 of the face, or any of the other measurement sites described herein, to the plane A substantially defined by the temperature measurement device 10. Such a determination may comprise a proximity determination. In particular, the distance range characterized by the distance D may correspond to and/or may be substantially equivalent to the length of the fields of view 19 associated with the sensors 18. Accordingly, determining at step: 202 that the temperature measurement device 10 is located within such a distance range may comprise determining that the portion 34 of the face and/or locations 36 on the portion 34 of the face are disposed within a field of view $19a \ldots 19n$ of at least one of the sensors 18.

In example embodiments, determining that the temperature measurement device 10 is located within such a distance range at step: 202 may include the first sensor 12 emitting a beam and/or a field of infrared radiation, at least a portion of which impinges on the portion 34 of the face. The first sensor 12 may also collect at least a portion of such emitted radiation, and may determine the distance D between, for example, the first sensor 12 and the plane B based on the collected radiation. The first sensor 12 may also provide one or more signals to the controller 30 indicative of the collected radiation and/or of the corresponding distance D. Alternatively and/or in addition, at step: 202 any other metric or process may be used by the controller 30 to determine whether the device 10 is within an acceptable sensing range and/or field of view of the sensors 18. For example, instead of determining the distance D between the first sensor 12 and the plane B at step: 202, the imaging device 16 may be utilized to capture one or more images of the face of the patient. The imaging device 16 may send one or more signals to the controller 30 containing information indicative of the image, and the controller 30 and/or the image processors associated therewith may determine whether the device 10 is within a field of view of the sensors 18 based on such information. For instance, if the image processors are able to identify one or more portions of the face, such as one or more of the locations 36, the controller 30 may determine that the device 10 has been properly positioned relative to the patient 14 to determine surface temperatures of the locations 36.

At step: 204, the controller 30 and/or the first sensor 12 may determine whether the temperature measurement device 10 is disposed within one or more alignment ranges relative to the plane B, and such alignment ranges may include one or more of the preferred angular alignment ranges F, G described above. For example, the first sensor 12 may determine whether the device 10 is disposed between a minimum angle $\alpha_b$ and a maximum angle $\alpha_c$ defined by the plane B and a line normal to the plane A. Such angles $\alpha_a$, $\alpha_c$ are described above with respect to the top view shown in FIG. 5. Additionally, the first sensor 12 may determine whether the device 10 is disposed between a minimum angle $\mu_b$ and a maximum angle $\mu_c$ defined by the plane B and a line normal to the plane A. Such angles $\mu_a$, $\mu_c$ are described above with respect to the side view shown in FIG. 6. Further, as noted above, such angles $\alpha$, $\mu$ may further define the fields of view 19 of the sensors 18, and the plane B may be substantially defined by any of the measurement sites described herein. Thus, determining that the temperature measurement device 10 is within one or more of the alignment ranges F, G at step: 204 may comprise a further confirmation that at least one of the first location 36a is disposed within the field of view 19a of the sensor 18a, and that the second location 36b is disposed within the field of view 19b of the sensor 18b. It is understood that the determinations made at step: 204 may be made by the first sensor 12 and/or the controller 30 substantially simultaneously with the determinations made at step: 202.

In example embodiments, the imaging device 16 and/or the controller 30 may assist in generating a visual and/or thermal image of the patient 14, and such an image 42 may be displayed by the display 20 of the temperature measurement device 10. Such an image 42 may be displayed on the display 20 before, during, and/or after the determinations described above with respect to steps: 202, 204 have been made. Additionally, such an image 42 may comprise a real time image and/or video of the patient 14, and the image 42 may be displayed on the display 20 throughout the various temperature determination methods described herein.

At step: 206, the display 20, the signal device 22, and/or the controller 30 may provide one or more indications to a user of the temperature measurement device 10 that the device 10 is located within the distance range described above with respect to step: 202. At step: 206, the display 20, the signal device 22, and/or the controller 30 may also provide one or more indications indicating that the temperature measurement device 10 is located within one or more of the alignment ranges F, G described above with respect to step: 204. As described above with respect to FIG. 3, such indications may include, for example, a first visual indication 44a substantially overlaying the first location 36a on the portion 34 of the face shown in the image 42, and a second visual indication 44b substantially overlaying the second location 36b on the portion 34. In such embodiments, the image 42 may be displayed on the display 20 throughout the temperature determination methods described herein, and at least one of the indications 44 may be displayed in the image 42 in response to at least one of the determinations described above with respect to steps: 202, 204.

One or more of the indications 44 described above may prompt the user of the device 10 to provide one or more inputs. For example, in embodiments in which one or more of the indications 44 is indicative of the device 10 being disposed at an acceptable distance D and/or within an acceptable alignment range F, G relative to the patient 14 (i.e., relative to the plane B), the user may actuate one or more of the user interfaces 24 or the display 22 direct one or more of the sensors 18 to determine the temperatures of respective locations 36 on the portion 34 of the face. It is understood that such inputs may be provided via the display 20 in embodiments in which the display 20 comprises a touch screen. Alternatively, in further embodiments the sensors 18 may automatically determine the temperature of respective locations 36 on the portion 34 of the face in response to the determinations made at one or more of steps: 202, 204. In such embodiments, step: 208 may be omitted.

At step: 210, the first sensor 12 and/or the controller 30 may determine one or more physical attributes of the patient 14. For example, at step: 210 the first sensor 12 may determine at least one of a distance between the first location 36a and the second location 36b, a distance between at least one of the first and second locations 36a, 36b and a third location 36c on the face of the patient 14, and one or more dimensions of the ear of the patient 14, such as a height H of the ear. The first sensor 12 may provide one or more signals to the controller 30 indicative of one or more such distances and/or dimensions, and the controller 30 may determine one or more of the physical attributes of the patient 14 described above based on such signals. Additionally, the imaging device 16 may assist in generating the image 42 described above, and the controller 30 and/or the image processor thereof may utilize the image 42 to determine the physical attributes at step: 210. It is understood that such physical attributes may be indicative of, for example, the age, gender, ethnicity, and/or other characteristics of the patient 14. Further, the controller 30 may automatically select one or more operating modes of the temperature measurement device 10 based on the physical attribute determined at step: 210. Selecting such an operating mode may include, for example, selecting one or more algorithms, neural networks, lookup tables, and/or other like components or protocols for use in determining a temperature of the patient 14.

For example, if the controller 30 determines, at step: 210, that the patient 14 is an adult, the controller 30 may, in response to the determination, automatically utilize one or more temperature determination algorithms tailored toward treatment and/or diagnosis of adult patients. Alternatively, if the controller 30 determines that the patient 14 is a pediatric patient, the controller 30 may, in response to the determination, automatically utilize one or more temperature determination algorithms tailored toward treatment and/or diagnosis of pediatric patients. A similar "tailored" algorithm and/or process may be employed by the temperature measurement device 10 in response to the determination of patient gender and/or ethnicity. Accordingly, one or more temperatures of the patient 14, such as a core temperature of the patient 14, may be determined based on the operating mode selected by the controller 30. Further, in such embodiments the controller 30 may automatically select an output type based on the one or more physical attributes determined at step: 210. For example, upon determining that the patient 14 is a pediatric patient, the controller 30 may, in response, select one or more algorithms, neural networks, look-up tables, and/or other like protocols having an output comprising a temperature corresponding to an axillary temperature output. It is understood that the controller 30 may select such an output type (i.e., an axillary temperature) since axillary temperatures are standard when treating and/or monitoring pediatric patients. Further, in such embodiments the physical attribute of the patient 14 may be entered, selected, and/or otherwise provided by the user of the device 10 at step: 210.

At step: 212 at least one of the sensors 18, such as the sensor 18a, and/or the controller 30 may determine a first temperature corresponding to the first location 36a on the portion 34 of the face of the patient 14. Additionally, at step: 212 at least one of the sensors 18, such as the sensor 18b, and/or the controller 30 may determine a second temperature corresponding to the second location 36b on the portion 34 of the face of the patient 14. In an example embodiment, the first location 36a may comprise a point or an area on the left inner-canthal region of the patient 14, and the second location was 36b may comprise a point or an area on the right inner-canthal region of the patient 14. In example embodiments, the portion 34 of the face used to obtain the first and second temperatures described herein may comprise a different measurement site than that used to determine at least one of the distance range and the angular alignment ranges F, G described above with respect to steps: 202 and 204. For example, while the forehead of the patient 14 may be used for the distance range determination at step: 202, locations 36 on the inner-canthal region and/or other like portions 34 of the face may be used for the temperature determinations at step: 212. Additionally, in embodiments in which at least one of the sensors 18 comprises an infrared sensor, the sensors 18 may collect radiation emitted by the respective locations 36, and may determine corresponding first and second temperatures based on such collected radiation. In such embodiments, the sensors 18 may determine the first and second temperatures at step: 212 without contacting the patient 14. The sensors 18 may also provide one or more signals to the controller 30 indicative of the first and second temperatures determined at step: 212.

At step: 214, the controller 30 may determine a third temperature of the patient 14 based on at least, for example, the first and second temperatures determined at step: 212. Such a third temperature may comprise any of the temperatures described herein, and in some embodiments, the third temperature determined at step: 214 may comprise a core temperature. In some embodiments, the third temperature may also be determined based at least partially on, for example, one or more of the physical attributes determined at step: 210. For example, at step: 214 at least one of the first and second temperatures may be utilized as inputs to one or more of the algorithms, neural networks, lookup tables, and/or other components selected based on the one or more physical attributes determined at step: 210. At least one of the sensors 18 may also determine, for example, an ambient temperature of the environment in which the temperature measurement device 10 is being used. In such embodiments, the ambient temperature may also be utilized as an input to such components at step: 214. In such embodiments, the third temperature determined at step: 214 may comprise an output of such components.

In example embodiments, the controller 30 may assign an arithmetic bias and/or other like weight factor to one or both of the first and second temperatures and/or the ambient temperature. Such a weight factor may be indicative of, for example, a priority of one of the determined temperatures relative to the other determined temperature, and such a relative priority may be useful when determining the core temperature of the patient 14 at step: 214. Such a weight factor may comprise, for example, a constant and/or other like coefficient associated with the one or more determined temperatures, and such coefficients may be part of a core temperature determination algorithm employed by the controller 30. The controller 30 may determine and/or associate such a weight factor with one or more of the determined temperatures described herein by using one or more weight factor look-up tables and/or weight factor data maps stored in the memory 32 of the controller 30. Moreover, the controller 30 may be configured to modify one of the determined temperatures based on the other determined temperature and the weight factor assigned and/or otherwise associated with at least one of the determined temperatures. Such a modification may be based on the weight factor associated with one or both of the determined temperatures, and such weight factors may be indicative of the relative correlation between such temperatures and the actual core temperature of the patient 14. Moreover, such a modification may be performed by nature of the one or more algorithms employed to determine the core temperature of the patient 14.

At step: 214 the third temperature of the patient 14 may also be communicated to the user. For example, as shown in FIG. 3, one or more of the first and second temperatures 46b, the ambient temperature 46d, and/or the core temperature 46c may be shown on the display 20. Additionally and/or alternatively, one or more such temperatures may be provided to one or more of the remote components 28 via the communication device 26 of the temperature measurement device 10. It is understood that in some embodiments, one or more of the steps illustrated in FIG. 7 may be combined and/or performed in a different order. For example, it is understood that data including the first and second temperatures described above with respect to step: 212 and/or information related to the physical attributes discussed with respect to step: 210 may be collected during any of the steps shown in FIG. 7. In still further embodiments, one or more of the steps illustrated in FIG. 7 may be omitted. For example, in further embodiments at least one of steps: 202 and 204 may be omitted without deviating from the various example temperature determinations described herein.

Such noncontact-based methods of temperature determination may be useful in a variety of applications. Such applications may include initial and/or patient intake screening, and situations in which the patient is uncooperative or unconscious. Such applications may also include situations in which temperature determination through traditional contact-based methods is outside of a designed temperature range of operation or may place the user at an elevated risk of contact with, for example, germs, viruses, contagious disease, patient bodily fluids, and/or other like substances or contaminants.

Other embodiments of the present disclosure will be apparent to those skilled in the art from consideration of the specification and practice of the embodiments described herein. For example, in example embodiments the temperature measurement device 10 of the present disclosure may include one or more ports, connectors, terminals, and/or other like connection devices configured to enable communication between the temperature measurement device 10 and one or more separate devices. It is intended that the specification and examples be considered as example only, with a true scope and spirit of the present disclosure being indicated by the following claims.

What is claimed is:

1. A method of determining a temperature of a patient, comprising:
    determining that a temperature measurement device is located within at least one of a distance range and an alignment range of a first portion of a measurement site of the patient;
    providing an indication to a user of the device that the device is located within the at least one of the distance range and the alignment range;
    determining, with the device, a first temperature of a first location on at least one of the first portion and a second portion of the measurement site, without contacting the patient with the device;
    determining, with the device, a second temperature of a second location on at least one of the first portion and the second portion of the measurement site, without contacting the patient with the device, wherein the second location is different from the first location; and
    determining a third temperature of the patient based on the first and second temperatures.

2. The method of claim 1, wherein the second portion of the measurement site comprises an inner-canthal region of the patient.

3. The method of claim 1, further including determining at least one of the first location is within a field of view of a first sensor of the device and the second location is within a field of view of a second sensor of the device.

4. The method of claim 3, wherein the field of view of at least one of the first and second sensors is characterized by an angle equal to between approximately 5 degrees and approximately 15 degrees.

5. The method of claim 1, wherein the distance range is between approximately 6 inches and approximately 14 inches, and wherein the distance range extends from a plane substantially defined by the first portion of the measurement site to a plane substantially defined by the device.

6. The method of claim 1, further including receiving an input from the user in response to the indication, and determining at least one of the first temperature and the second temperature in response to the input.

7. The method of claim 1, further including displaying an image of the patient, wherein the indication is illustrated in the image.

8. The method of claim 7, further including displaying at least one of the temperature of the first location, the temperature of the second location, and the third temperature in the image.

9. The method of claim 7, wherein the indication illustrated in the image comprises a first indication indicating that the first location is within a field of view of a first sensor of the device, and a second indication indicating that the second location is within a field of view of a second sensor of the device.

10. The method of claim 1, further including determining a physical attribute of the patient with at least one sensor of the device, and automatically selecting an operating mode of the device based on the attribute, wherein the third temperature comprises a core temperature determined based on the operating mode.

11. The method of claim 10, wherein the attribute comprises at least one of a distance between the first location and the second location, a distance between at least one of the first and second locations and a third location on the measurement site, and a dimension of an ear of the patient.

12. A temperature measurement device, comprising:
a first sensor configured to determine that the device is located within at least one of a distance range and an alignment range of a first portion of a measurement site of a patient;
at least one additional sensor, the at least one additional sensor being configured to determine a first temperature of a first location on at least one of the first portion and a second portion of the measurement site and a second temperature of a second location on at least one of the first portion and the second portion of the measurement site,
wherein the at least one additional sensor determines the first and second temperatures without contacting the patient, and
wherein the first and second temperatures are determined in response to the first sensor determining that the device is located within the at least one of the distance range and the alignment range; and
a controller in communication with the first sensor and the at least one additional sensor, the controller being programmed to determine a third temperature of the patient based on the first and second temperatures.

13. The device of claim 12, wherein the first sensor comprises a proximity sensor, and wherein the distance range extends from a plane substantially defined by the device to a plane substantially defined by the first portion of the measurement site.

14. The device of claim 12, wherein the at least one additional sensor comprises a first infrared sensor configured to determine the first temperature and a second infrared sensor separate from the first infrared sensor, the second infrared sensor configured to determine the second temperature.

15. The device of claim 14, wherein the first and second infrared sensors have respective fields of view characterized by respective angles equal to between approximately 5 degrees and approximately 15 degrees, and wherein the distance range is between approximately 6 inches and approximately 14 inches.

16. The device of claim 12, further including a user interface in communication with the controller, the user interface configured to receive an input from a user of the device in response to determining that the device is located within the at least one of the distance range and the alignment range, wherein the at least one additional sensor is configured to determine at least one of the first temperature and the second temperature in response to the input.

17. The device of claim 12, further including a display in communication with the controller, the display configured to provide an indication to a user of the device that the device is located within the at least one of the distance range and the alignment range, and to display an image of the patient, wherein the indication is illustrated in the image.

18. The device of claim 17, wherein the at least one additional sensor comprises a second sensor and a third sensor separate from the second sensor, and wherein the indication illustrated in the image comprises a first indication indicating that the first location is within a field of view of the second sensor, and a second indication indicating that the second location is within a field of view of the third sensor.

19. The device of claim 12, wherein the device is configured to determine a physical attribute of the patient, the controller is configured to automatically select an operating mode of the device based on the attribute, and the attribute comprises at least one of a distance between the first location and the second location, a distance between at least one of the first and second locations and a third location on the measurement site, and a dimension of an ear of the patient.

* * * * *